United States Patent [19]

Ohmori et al.

[11] Patent Number: 5,541,162
[45] Date of Patent: Jul. 30, 1996

[54] GLUTATHIONE DERIVATIVES

[75] Inventors: Shinji Ohmori, Okayama; Kazumi Ogata, Toyonaka; Takahiro Sakaue, Itami, all of Japan

[73] Assignee: Senju Pharmaceutical Co., Ltd., Osaka, Japan

[21] Appl. No.: 198,373

[22] Filed: Feb. 18, 1994

Related U.S. Application Data

[63] Continuation of Ser. No. 41,124, Mar. 3, 1993, abandoned, which is a continuation of Ser. No. 768,966, filed as PCT/JP91/00217, Feb. 15, 1991, abandoned.

[30] Foreign Application Priority Data

Feb. 17, 1990 [JP] Japan .................................. 2-36745
May 23, 1990 [JP] Japan .................................. 2-133600

[51] Int. Cl.$^6$ .......................... A61K 38/06; C07K 5/093
[52] U.S. Cl. .......................... 514/18; 530/331; 530/332
[58] Field of Search ................ 514/18, 562; 530/331, 530/332

[56] References Cited

U.S. PATENT DOCUMENTS

| | | | |
|---|---|---|---|
| 4,537,718 | 8/1985 | Schachter et al. | 436/518 |
| 4,710,489 | 12/1987 | Meisler | 514/18 |
| 5,081,149 | 1/1992 | Ohmori et al. | 514/534 |
| 5,135,952 | 8/1992 | Ohmori et al. | 514/547 |
| 5,232,913 | 8/1993 | Ohmori et al. | 530/331 |
| 5,274,177 | 12/1993 | Ohmori et al. | 530/331 |
| 5,378,692 | 1/1995 | Ohmori et al. | 514/19 |

OTHER PUBLICATIONS

Biochemistry, vol. 15, No. 19, Issued 1976, Morrison et al, "Maleyl–Acetone Cis–Trans–Isomerase . . .", pp. 4228–4233.

Research in Experimental Medicine, vol. 190, No. 6, Issued Dec. 1990, Miyazaki et al, "Enhancing Effect of S–(1, 2–Dicarboxyethyl) Glutathione", pp. 381–387.

Z. Naturforsch., vol. 42C, Issued 1987, Frister et al, "Ringoffnung–Sreaklionen an Bioreaktiven . . .", pp. 603–612.

Agric Biol. Chem., vol. 49, No. 8, Issued 1985, Kuninori et al, "Some Properties of Diastereomers . . .", pp. 2453–2454.

Atarashii Ganka, vol. 7, No. 3, Issued 1990, Mio et al, "Inhibitory Effect of S–(1,2–Dicarboxyethyl) Glutathione . . .", pp. 407–409.

Biochem. J. vol. 109, Issued 1968, Boyland et al, "Enzymes Catalyzing Conjugations of Gultathione . . .", pp. 651–661.

J. Clear Chem., Clin. Biochem., vol. 22 (4) (1984) Tsuboi et al. pp. 285.

Primary Examiner—Jeffrey E. Russel
Attorney, Agent, or Firm—Wenderoth, Lind & Ponack

[57] ABSTRACT

An antiinflammatory, antiallergic or hepatic disorders inhibitory agent containing a compound of the following formula or a pharmaceutically acceptable salt thereof as an active ingredient $$\text{HOOC}-\text{CH}-\text{CH}_2\text{CH}_2\text{CONH}-\text{CH}-\text{CONH}-\text{CH}_2-\text{COOR}_1$$
$$\phantom{\text{HOOC}-}\overset{|}{\text{NH}_2} \phantom{\text{CH}_2\text{CH}_2\text{CONH}-} \overset{|}{\text{CH}_2-\text{S}(\text{CH}_2)_n\text{CH}-\text{COR}_2}$$
$$\phantom{\text{HOOC}-\text{CH}-\text{CH}_2\text{CH}_2\text{CONH}-\text{CH}-\text{CONH}-}\overset{|}{\text{CH}_2-\text{COR}_3}$$

(wherein n represents 0 or 1; $R_1$ means hydrogen or an alkyl group; $R_2$ and $R_3$ are the same or different and independently mean a hydroxyl group, a lower alkoxy group or an amino group or $R_2$ and $R_3$ together form an imino group; provided that $R_1$ means an alkyl group where n=0 and $R_2$ and $R_3$ are the same or different and independently mean a hydroxyl group or a lower alkoxy group).

3 Claims, 3 Drawing Sheets

GLUTATHIONE DERIVATIVES

This application is a continuation of now abandoned application Serial No. 08/041,124, filed Mar. 31, 1993, which is a continuation of now abandoned application Ser. No. 07/768,966, filed as PCT/JP91/00217, Feb. 15, 1991.

TECHNICAL FIELD

The present invention relates to novel and useful glutathione derivatives. More particularly, the invention relates to a glutathione (or an ester thereof)-S-succinic acid or a derivative thereof, a process for production thereof, and an antiinflammatory, antiallergic or hepatic disorders inhibitory composition containing said compound or derivative.

BACKGROUND ART

Heretofore known are various glutathione derivatives. Among them, S-(α,β-dicarboxyethyl)glutathione is a substance found in the body which D. H. Calam and S. G. Waley (Biochem. J. 86, 226, 1963) discovered in the bovine crystalline lens but its physiological activity remained to be known for certain. However, the inventors of the present invention found that this compound has platelet aggregation inhibitory, antiinflammatory, antiallergic, antitumor and hepatic disorders inhibitory activities (Japanese Kokai Tokkyo Koho No. 63-8337 (1988), and Japanese Patent Application No. 1-79956 (1989), No. 1- 183484 (1989), No. 1-251534 (1989) and No. 1-256370 (1989).

In search of glutathione derivatives which would be more efficiently absorbed by tissues, the inventors of the present invention synthesized new glutathione derivatives using glutathione (or monoesters thereof) and maleic acid or itaconic acid or an ester, amide or imide thereof respectively, and discovered that these compounds have excellent pharmacological activities. This discovery and subsequent research resulted in the present invention.

DISCLOSURE OF THE INVENTION

The present invention relates to (1) a compound of the following formula

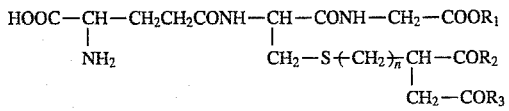

(wherein n represents 0 or 1; $R_1$ means hydrogen or an alkyl group; $R_2$ and $R_3$ are the same or different and independently mean a hydroxyl group, a lower alkoxy group, an amino group or an imino group; provided that $R_1$ means an alkyl group where n=0 and $R_2$ and $R_3$ are the same or different and independently mean a hydroxyl group or a lower alkoxy group) or a pharmaceutically acceptable salt thereof, (2) a process for producing the same, and (3) an antiinflammatory, antiallergic or hepatic disorders inhibitory composition containing said compound or salt as an active ingredient.

Referring to the above formula, $R_1$ means hydrogen or a lower alkyl group and the number of carbon atoms in said alkyl group is preferably 1 through 10. The carbon chain of said alkyl group may be straight, branched or cyclic and may also contain a ring structure. Thus, the alkyl group includes, among others, methyl, ethyl, n-propyl, i-propyl, cyclopropyl, n-butyl, t-butyl, sec-butyl, n-pentyl, 1-ethylpropyl, i-pentyl and benzyl.

$R_2$ and $R_3$ in the above formula may be the same or different and each means a hydroxyl group, a lower alkoxy group, an amino group or an imino group. The lower alkoxy group includes, among others, methoxy, ethoxy, propoxy, isopropoxy, butoxy, isobutoxy, sec-butoxy, tert-butoxy, pentyloxy, isopentyloxy, tert-pentyloxy, neopentyloxy, 2-methylbutoxy, 1,2-dimethylpropoxy, 1-ethylpropoxy and so on. The amino and imino groups may be substituted by alkyl groups, for instance.

In the pharmaceutical composition of the present invention, the compound can be used in the form of free acid or in the form of a pharmaceutically acceptable nontoxic salt such as an alkali metal salt, e.g. sodium salt, potassium salt, etc., or an alkaline earth metal salt, e.g. calcium salt, magnesium salt so on. These salts may be those involving all the carboxyl groups available in the compound or those involving fewer of the carboxyl groups. All of such salts can be selectively used in the preparation of the pharmaceutical composition of the invention.

The process for producing the compound in accordance with the present invention is as follows. First, either glutathione or a glutathione monoester (γ-glutamylcystinylglycine ester) obtainable by reacting glutathione with the corresponding alcohol in the presence of an acid, such as sulfuric acid, is reacted with maleic acid or iraconic acid or a derivative thereof in water or an aqueous medium at a pH of about 4–8 with stirring at room temperature or under warming. This reaction readily goes to completion. The reaction mixture is purified by column chromatography or by recrystallization from an appropriate solvent to isolate the desired compound. The derivative of maleic acid or iraconic acid may be a diester, monoester, diamide, monoamide, imide or N-alkylamine, or even a mixture thereof.

The compounds obtainable by the above process invariably contain asymmetric carbon atoms and, as such, may occur as optical isomers and any of such optically active compounds as well as mixtures thereof are useful for the invention.

The inflammatory diseases which can be treated with the pharmaceutical composition of the present invention includes, among others, rheumatoid arthritis, spondylosis deformans, osteoarthritis, lumbago, gout attack, acute otitis media, cystiris, prostatitis, toothache, uveitis and sinuitis.

The allergic diseases in which the pharmaceutical composition of the invention can be indicated include, among others, bronchial asthma, pollinosis, allergic thiniris, alimentary allergic gastritis, allergic diarrhea, ulcerative colitis, stomatitis, periarteritis nodosa, obstructive endarteritis, endocarditis, urticaria, eczema, contact dermatitis, phlyctena, sympathetic ophthalmitis, allergic conjuctivitis and allergic keratitis. The pharmaceutical composition of the invention can be used with advantage in the treatment of such diseases.

Furthermore, the pharmaceutical composition of the present invention is effective in preventing onset of acute or chronic hepatic diseases, inhibits elevation of GOT and GPT values, and is useful for the prophylaxis and therapy of acute or chronic hepatitis. It can also be used with success in the prevention and treatment of hepatocirrhosis. For example, this pharmaceutical composition can be advantageously employed for hepatic disorders induced by drugs such as acetaminophen.

As mentioned just above, the pharmaceutical composition of the present invention can be used as a therapeutic agent for inflammatory or allergic diseases or as a hepatic disorders inhibitory agent, either orally or non-orally. The applicable dosage forms include, among others, a variety of solid preparations such as tablets, granules, powders, capsules, ointments, etc. and a variety of liquid preparations such as eye-drops, ear-drops, nasal solutions, injections and so on. These dosage forms can be selectively adopted with reference to the type and site of the disease to be treated and be manufactured by the per se known procedures. These compositions may contain a variety of appropriate additives commonly employed in the pharmaceutical industry, such as the binder, disintegrating agent, thickener, dispersing agent, reabsorption promoter, corrigent, buffer, surfactant, solubilizer, preservative, emulsifier, isotonizing agent, stabilizer, pH adjusting agent and other excipients.

While the recommended dosage of the active ingredient is dependent on the particular species of compound, the type of diseases, the patient's age and body weight, the dosage form chosen and the clinical condition to be dealt with, the dosage recommended for injection is about 1–500 mg/dose/day adult and that for oral administration is about 10–2000 mg/dose/adult to be administered a few times a day. For local administration, the recommended dosage is about 0.1 to 5 (w/v) %.

The pharmaceutical composition of the invention may contain one or more species of the compound according to the therapeutic objective and where necessary.

Unless contrary to the object of the invention, the pharmaceutical composition of the invention may contain other active ingredients having different pharmacological actions from those of the compound of the invention.

BEST MODE OF WORKING THE INVENTION

The following examples and formulation examples are further illustrative of the present invention.

EXAMPLE 1

γ-L-Glutamyl-[S-(1,2-dicarbethoxyethyl)]-L-cystinylglycine isopropyl ester

[S-(1,2-Dicarbethoxyethyl)glutathione isopropyl ester]

[$R_1=C_3H_7$, $R_2=R_3=OC_2H_5$, n=0]

In 50 ml of water is suspended 4.0 g of γ-L-glutamyl-L-cystinylglycine isopropyl ester sulfate (hereinafter referred to as "GS-isopropyl ester sulfate"), and 2N-sodium hydroxide is then added dropwise to adjust the suspension to pH 7.0 for dissolution. Then, 2.0 g of diethyl maleate is added and the mixture is stirred at room temperature for 3 hours. The mixture is acidified with 1 ml of acetic acid and concentrated, followed by addition of ethanol and ethyl acetate. The resulting inorganic salt is filtered off and the solvent is distilled off. The residue is dissolved in ethyl acetate and n-hexane is added to the solution. The resulting colloidal crystals are recovered by filtration and recrystallized from ethyl acetate-n-hexane. Yield, 3.8 g.

TLC, silica gel Rf=0.55 (n-butanol-acetic acid-water =4:1:1)

Elemental analysis for $C_{21}H_{35}O_{10}N_3 \cdot \frac{1}{2}H_2O$ Calcd. (%) C, 47.54; H, 6.84; N, 7.92 Found (%) C, 47.42; H, 6.75; N, 7.87

Figure 1:
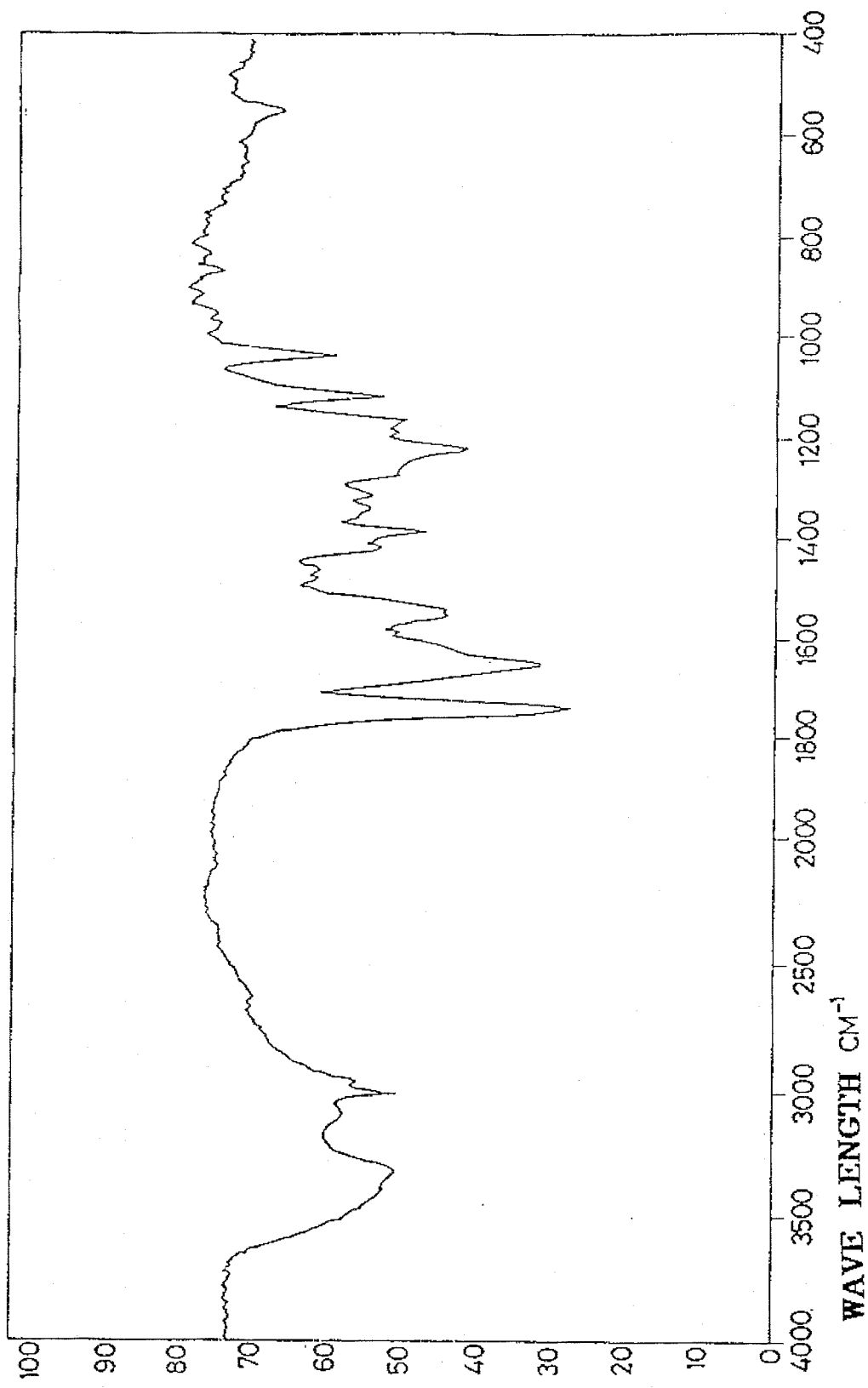
FIG. 1 is an IR spectrum of S-(1,2-dicarbethoxyethyl)glutathione isopropyl ester.

The IR spectrum of this compound is shown in FIG. 1.

EXAMPLE 2

S-(1,2-Dicarbo-n-butoxyethyl)glutathione isopropyl ester

[$R_1=C_3H_7$, $R_2=R_3=OC_4H_9$, n=0]

In 50 ml of water is suspended 4.0 g of GS-isopropyl ester sulfate and the suspension is adjusted to pH 7.0 with 2N-sodium hydroxide as in Example 1. Then, 2.5 g of di-n-butyl maleate and 50 ml of ethanol are added and the mixture is stirred at room temperature for 12 hours. The solvent is then distilled off and the residue is extracted with ethyl acetate, washed with water and distilled to remove the solvent. To the residue is added petroleum benzin and the resulting white crystals are recovered by filtration and recrystallized from ethyl acetate-petroleum benzin to give 3.8 g of white crystals.

TLC, silica gel Rf=0.60 (n-butanol-acetate acid-water= 4:1:1)

Elemental analysis for $C_{25}H_{43}O_{10}N_3S \cdot \frac{1}{2}H_2O$ Calcd. (%) C, 51.18; H, 7.56; N, 7.16 Found (%) C, 51.24; H, 7.41; N, 7.07

EXAMPLE 3

S-(1,2-Dicarbamoylethyl)glutathioneisopropyl ester

[$R_1=C_3H_7$, $R_2=R_3=NH_2$, n=0]

Using 4.0 g of GS-isopropyl ester sulfate and 1.5 g of maleamide, the reaction procedure of Example 1 is followed. The reaction mixture is concentrated and subjected to Sephadex G-10 column chromatography (eluent: ethanol-water=1:1). The crystals thus obtained are recrystallized from water-ethanol to give 3.7 g of white colloidal crystals.

Rf=0.22 (n-butanol-acetic acid-water=4:1:1)

Elemental analysis for $C_{17}H_{29}O_8N_5S \cdot \frac{1}{2}H_2O$ Calcd. (%) C, 43.21; H, 6.40; N, 14.82 Found (%) C, 43.12; H, 6.39; N, 14.66

EXAMPLE 4

S-[(1,2-Dicarboximido)ethyl]glutathione isopropyl ester

[$R_1=C_3H_7$, $R_2R_3=NH$, n=0]

Using 4.0 g of GS-isopropyl ester sulfate and 1.3 g of maleimide, the reaction and workup procedure of Example 3 is followed to give 1.5 g of amorphous (colloidal) crystals.

Rf=0.37 (n-butanol-acetic acid-water=4:1:1)

Elemental analysis for $C_{17}H_{26}O_8N_4S$ Calcd. (%) C, 45.73; H, 5.8? ; N, 12.55 Found (%) C, 4S.61; H, 5.85; N, 12.28

Figure 2:
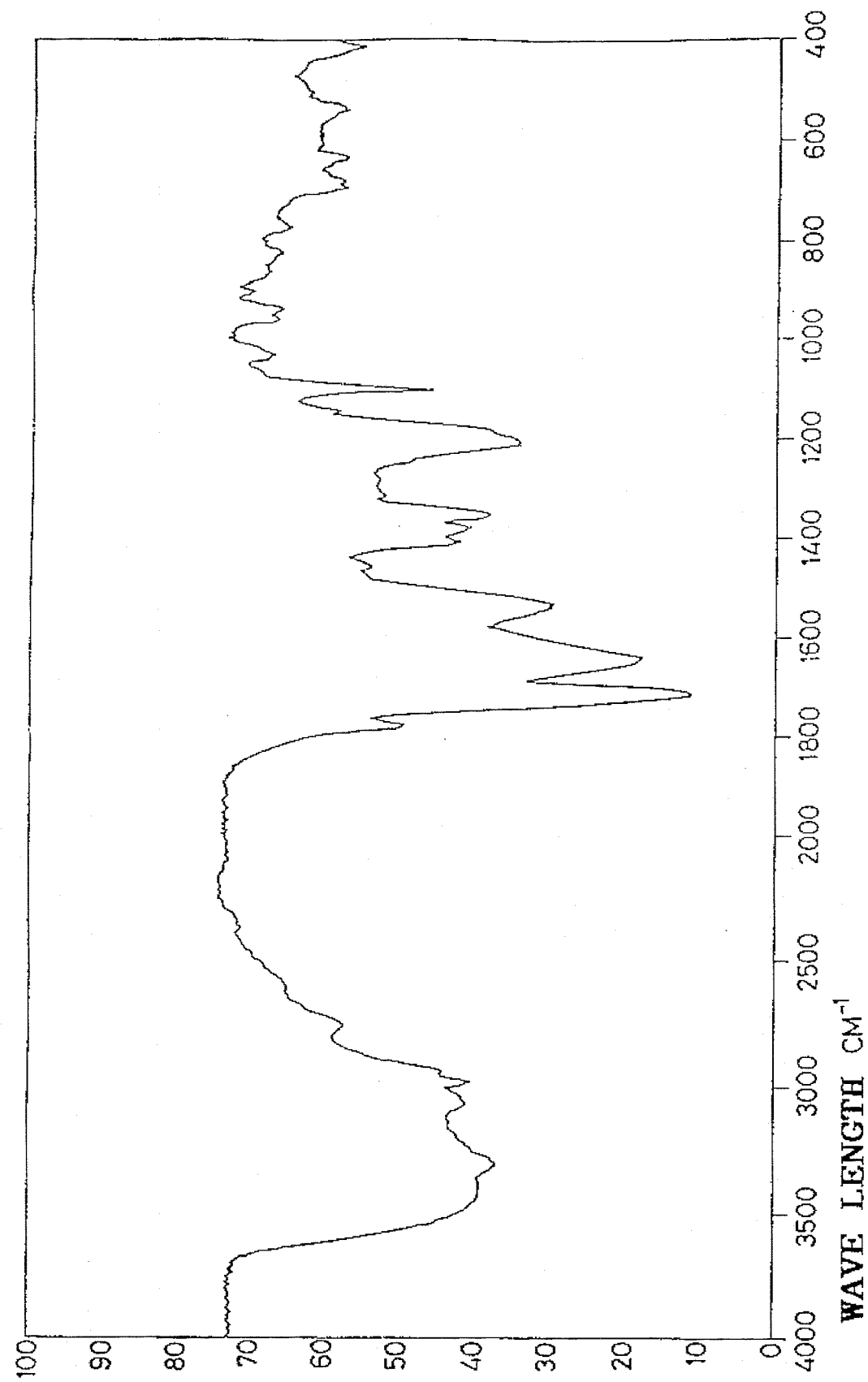
FIG. 2 is an IR spectrum of S-[(1,2-dicarboximido)ethyl]glutathione isopropyl ester.

The IR spectrum of this compound is shown in FIG. 2.

EXAMPLE 5

S-(1,2-Dicarboxyethyl)glutathioneisopropyl ester

[$R_1=C_3H_7$, $R_2=R_3=OH$, $n=0$]

Using 4.0 g of GS-isopropyl ester sulfate and 1.6 g of maleic acid, the procedure of Example 3 is followed to give 3.4 g of the desired compound as the Na salt.

TLC, silica gel Rf=0.25 (n-butanol-acetic acid-water= 4:1:1)

EXAMPLE 6

S-[1-(or 2)carboxy-2-(or 1)carbethoxyethyl]glutathione isopropyl ester

[$R_1=C_3H_7$, $R_2=OH$ or $OC_2H_5$, $R_3=OC_2H_5$ or $OH$, $n=0$]

Using 4.0 g of GS-isopropyl ester sulfate and 1.7 g of monoethyl maleate, the procedure of Example 3 is followed to give 2.7 g of white crystals.

TLC, silica gel Rf=0.36 (n-butanol-acetic acid-water= 4:1:1)

EXAMPLE 7

S-[1,2-Dicarbo-n-butoxyethyl)glutathione ethyl ester

[$R_1=C_2H_5$, $R_2=R_3=OC_4H_9$, $n=0$]

In 20 ml of ethanol is suspended 3.1 g of glutathione followed by dropwise addition of 0.8 ml of sulfuric acid under ice-cooling and stirring for dissolution. The mixture is stirred at room temperature for 3 hours and, then, allowed to stand in the refrigerator overnight. Then, 40 ml of water is added and the mixture is adjusted to pH 7.0 with 2N-sodium hydroxide solution. To this solution is added 2.7 g of di-n-butyl maleate and the mixture is stirred for 24 hours. The reaction mixture is then concentrated and ethanol is added. The inorganic salt is filtered off and the solvent is distilled off. Thereafter, the residue is treated as in Example 3 and recrystallized from ethyl acetate-isopropyl ether to give 3.1 g of amorphous colorless crystals.

TLC, silica gel Rf=0.57 (n-butanol-acetic acid-water= 4:1:1)

Elemental analysis for $C_{24}H_{41}O_{10}N_3S\cdot\frac{1}{2}H_2O$ Calcd. (4) C, 50.34; H, 7.39; N, 7.34 Found (4) C, 50.36; H, 7.35; N, 7.25

EXAMPLE 8

S-(1,2-Dicarbethoxyethyl)glutathione ethyl ester

The procedure of Example 7 is repeated except that diethyl maleate is used in lieu of dibutyl maleate.

TLC, silica gel Rf=0.48 (n-butanol-acetic acid-water= 4:1:1)

Figure 3:
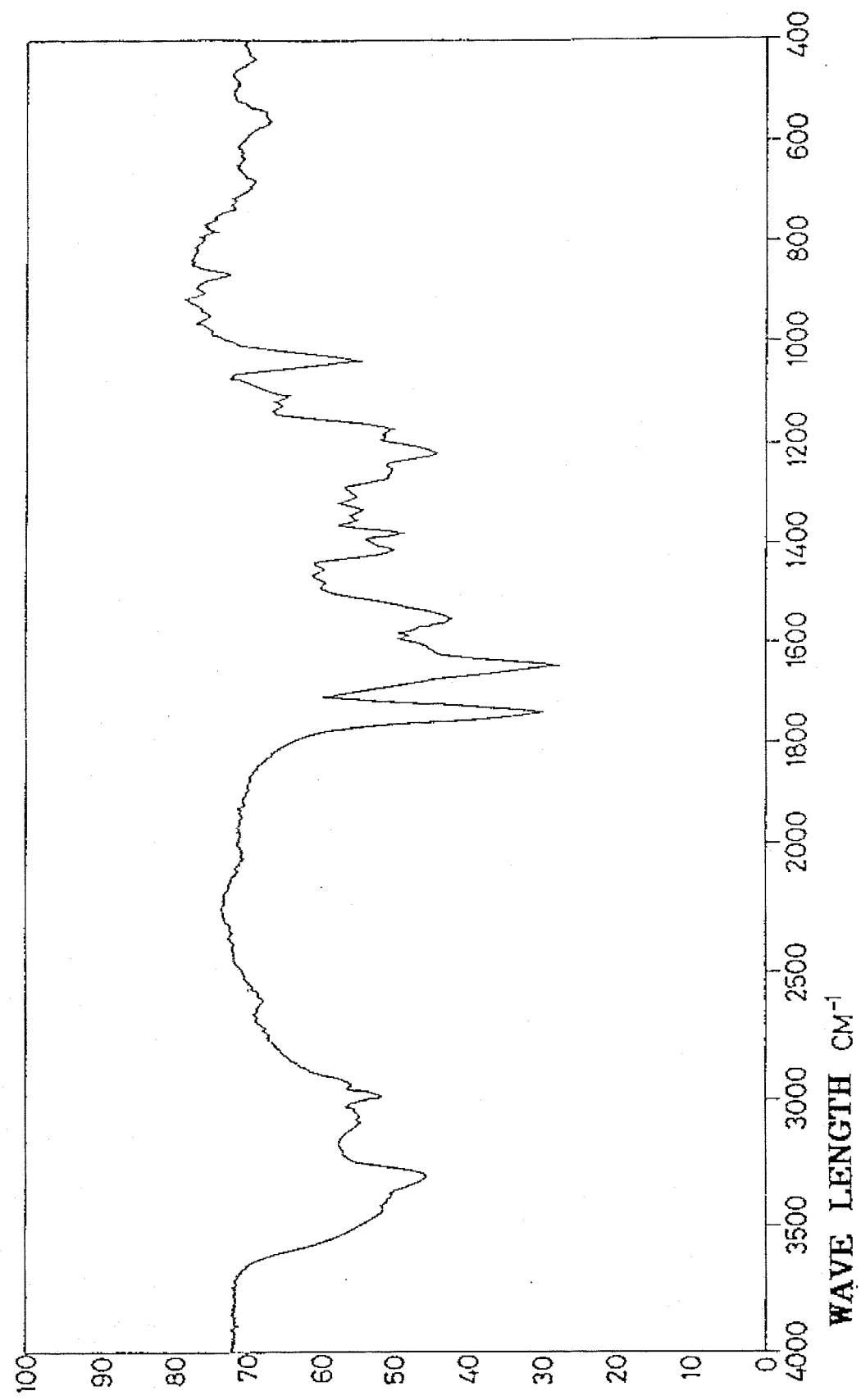
FIG. 3 is an IR spectrum of S-(1,2-dicarbethoxyethyl)glutathione ethyl ester.

The IR spectrum of this compound is shown in FIG. 3.

EXAMPLE 9

S-(1,2-Dicarbamoylethyl)glutathione

[$R_1=H$, $R_2=R_3=NH_2$, $n=0$]

In 150 ml of water is dissolved 9.2 g of glutathione and the solution is adjusted to pit 6.5 with 2N-sodium hydroxide. Then, 4.6 g of maleamide is added and the mixture is stirred for 24 hours. Then, 6.6 g of copper acetate is dissolved therein and the solution is allowed to stand, whereupon a bluish white copper salt seperates out. The crystals are recovered by filtration, rinsed with water and suspended in 200 ml of water. Then, hydrogen sulfide gas is bubbled through the suspension to precipitate the black copper sulfate. This precipitate is filtered off and the filtrate is concentrated. To the concentrate is added ethanol and the resulting crystals are recovered by filtration and recrystallized from water-ethanol to give 9.5 g of white crystals.

TLC, silica gel Rf=0.07 (n-butanol-acetic acid-water= 4:1:1)

Elemental analysis for $C_{14}H_{23}O_8N_5S\cdot H_2O$ Calcd. (%) C, 38.27; H, 5.73; N, 15.94 Found (%) C, 38.33; H, 5.51; N, 15.79

EXAMPLE 10

S-[(1,2-Dicarboximido)ethyl]glutathione

[$R_1=H$, $R_2R_3=NH$, $n=0$]

Using 9.2 g of glutathione and 3.5 g of maleimide, the procedure of Example 9 is followed to give 9.5 g of white crystals.

TLC, silica gel Rf=0.15 (n-butanol-acetic acid-water= 4:1:1)

Elemental analysis for $C_{14}H_{20}O_8N_4S$ Calcd. (%) C, 41.58; H, 4.99; N, 13.85 Found (%) C, 41.32; H, 4.95; N, 13.65

EXAMPLE 11

S-[N-Ethyl-2,5-dioxopyrrolidin-3-yl]glutathione

[$R_1=H$, $R_2=R_3=N-C_2H_5$, $n=0$]

The procedure of Example 9 is repeated using N-ethyl-maleimide in lieu of maleamide. White crystals, m.p. 190–191° (decomp.), yield 90%

EXAMPLE 12

S-[1-(or 2)Carboxy-2-(or 1)carbamoylethyl]glutathione

[$R_1=H$, $R_2=OH$ (or $NH_2$), $R_3=NH_2$ (or $OH$), $n=0$]

The reaction of Example 9 is repeated using 9.2 g of glutathione and 4.5 g of maleamic acid. In the reaction mixture is dissolved 6.6 g of copper acetate and the copper salt precipitated on addition of ethanol is recovered by filtration and treated to give white crystals. These crystals are dissolved in water and purified by Sephadex G-10 column chromatography (eluent: methanol-water=1:1) to give 6.9 g of white crystals.

TLC, silica gel Rf=0.05 (n-butanol-acetic acid-water= 4:1:1)

EXAMPLE 13

S-(1,2-Dicarboisopropoxyethyl)glutathione isopropyl ester

[$R_1=R_2=R_3=C_3H_7$, n=0]

The reaction and workup procedure of Example 2 is repeated using 4.0 g of GS-isopropyl ester sulfate and 2.4 g of diisopropyl maleate. Recrystallization from ethyl acetate-n-hexane gives 2.9 g of amorphous crystals.

TLC, silica gel Rf=0.56 (n-butanol-acetic acid-water= 4:1:1)

EXAMPLE 14

S-(1,2-Dicarboisobutoxyethyl)glutathione isopropyl ester

[$R_1=C_3H_7$, $R_2=R_3=C_4H_9$, n=0]

The reaction and workup procedure of Example 2 is repeated using 4.0 g of GS-isopropyl ester sulfate and 2.6 g of diisobutyl maleate. Recrystallization from ethyl acetate-n-hexane gives 2.5 g of amorphous crystals.

TLC, silica gel Rf=0.60 (n-butanol-acetic acid-water= 4:1:1)

Elemental analysis for $C_{25}H_{43}O_{10}N_3S$ Calcd. (%) C, 51.98; H, 7.50; N, 7.27 Found (4) C, 51.79; H, 7.46; N, 7.20

EXAMPLE 15

S-(2,3-Dicarbo-n-butoxypropyl)glutathione isopropyl ester $R_1=C_3H_7$, $R_2=R_3=C_4H_9$, n=1]

The reaction and workup procedure of Example 2 is repeated using 4.0 g of GS-isopropyl ester sulfate and 2.8 g of di-n-butyl itaconate. Recrystallization from ethyl acetate-petroleum benzin gives 2.5 g of white crystals.

TLC, silica gel Rf=0.55 (n-butanol-acetic acid-water= 4:1:1)

Elemental analysis for $C_{26}H_{45}O_{10}N_3S$ Calcd. (%) C, 52.78; H, 7.67; N, 7.10 Found (%) C, 52.65; H, 7.51; N, 7.12

EXAMPLE 16

Effect on Carrageenin-induced Conjunctival Edema

Method: Male Wistar rats (body weight about 120 g) purchased from Shizuoka Laboratory Animal Center were used as test animals.

Each animal was anesthesized with pentobarbital 6 mg/kg i.p. and a solution of the test substance in physiological saline was intravenously administered (30 mg/5 ml/kg). After 1 minute, 50 μl of a 1% solution of carrageenin in physiological saline was injected subconjunctivally. After 3 minutes, the rat was sacrificed and the carrageenin-induced conjunctival edema was weighed.

Results: The effect of nine glutathione derivatives on carrageenin-induced conjunctival edema was evaluated (Table 1). As a result, significant efficacy was found in compounds wherein n=0, $R_1=C_3H_7$ and $R_2=R_3=OH$, $OC_2H_5$ or $NH_2$ or $R_2R_3=NH$.

TABLE 1

Effect on carrageenin-induced conjunctival edema

| Test substance (n = 0) | Conjunctival edema weight (mg ± S.E) | % Inhibition |
|---|---|---|
| Physiological saline | 78.9 ± 4.3 | — |
| $R_1 = C_3H_7$, $R_2 = R_3 = OH$ | 63.9 ± 3.6 *1 | 19.0 |
| $R_1 = C_3H_7$, $R_2 = R_3 = OC_2H_5$ | 60.2 ± 1.2 *2 | 23.7 |
| $R_1 = C_3H_7$, $R_2 = R_3 = OC_4H_9$ | 77.4 ± 4.0 | 1.9 |
| $R_1 = C_3H_7$, $R_2 = R_3 = NH_2$ | 58.2 ± 1.4 *2 | 26.2 |
| $R_1 = C_3H_7$, $R_2R_3 = NH$ | 62.0 ± 1.6 *2 | 21.4 |
| Physiological saline | 70.9 ± 3.3 | — |
| $R_1 = H$, $R_2 = R_3 = NH_2$ | 67.1 ± 3.8 | 5.4 |
| $R_1 = H$, $R_2 = OH$ (or $NH_2$) $R_3 = NH_2$ (or OH) | 64.1 ± 4.2 | 9.6 |
| $R_1 = H$, $R_2R_3 = NH$ | 63.9 ± 4.1 | 9.9 |
| $R_1 = H$, $R_2R_3 = N-C_2H_5$ | 63.9 ± 3.6 | 9.9 |

The number of cases is 10. Significant difference from saline control: *1: p < 0.05, *2: p < 0.01

EXAMPLE 17

Effect on Rat Back Passive Anaphylactic Reaction

Method: Male Wistar rats (body weight about 130 g) purchased from Shizuoka Laboratory Animal Center were used as test animals. The back hair of each rat was clipped off and the antiserum was injected intradermally at the back. After 3 days, the test substance 30 mg/kg was injected into the caudal vein (control: physiological saline). One minute later, 1 ml of a 50:50 mixture of 1% egg white albumin and 2% Evans blue in physiological saline was intravenously administered as the antigen to induce a passive anaphylactic reaction. After 30 minutes, the rat was sacrificed, the stained area of the rat back was isolated the dye was extracted with 10 ml of formamide to determine the amount of the dye.

Results: The effect of nine glutathione derivatives on back anaphylactic reaction was evaluated (Table 2). As a result, significant efficacy was found in compounds wherein n=0, $R_1=C_3H_7$ and $R_2=R_3=OH$, $OC_2H_5$, $OC_4H_9$ or $NH_2$ and compounds wherein $R_1=H$ and $R_2=OH$ (or $NH_2$) or/and $R_3=NH_2$ (or OH) or $R_2R_3=NH$.

TABLE 2

Effect on rat back passive anaphylactic reaction

| Test substance (n = 0) | Absorbance | % Inhibition |
|---|---|---|
| Physiological saline | 0.873 ± 0.136 | — |
| $R_1 = C_3H_7$, $R_2 = R_3 = OH$ | 0.457 ± 0.055 *1 | 47.7 |
| $R_1 = C_3H_7$, $R_2 = R_3 = OC_2H_5$ | 0.484 ± 0.093 *1 | 44.6 |
| $R_1 = C_3H_7$, $R_2 = R_3 = OC_4H_9$ | 0.492 ± 0.094 *1 | 43.6 |
| $R_1 = C_3H_7$, $R_2 = R_3 = NH_2$ | 0.492 ± 0.083 *1 | 43.6 |
| $R_1 = C_3H_7$, $R_2 = R_3 = NH$ | 0.642 ± 0.141 | 26.5 |
| Physiological saline | 0.873 ± 0.136 | — |
| $R_1 = H$, $R_2 = R_3 = NH_2$ | 0.565 ± 0.162 | 35.3 |
| $R_1 = H$, $R_2 = OH$ (or $NH_2$) $R_3 = NH_2$ (or OH) | 0.494 ± 0.066 *1 | 43.4 |
| $R_1 = H$, $R_2R_3 = NH$ | 0.459 ± 0.104 *1 | 47.4 |
| $R_1 = H$, $R_2R_3 = N-C_2H_5$ | 0.514 ± 0.050 | 41.1 |

Mean ± S.E. The number of cases is 5. Significant difference from saline control: *1: p < 0.05

EXAMPLE 18

Effect on Acetaminophen-induced Liver Damage

Method: Male SD rats (body weights about 180 g) purchased from Shizuoka Laboratory Animal Center were used as test animals. The test substance was orally administered (0.5 mmole/kg), and after 1 hour, acetaminophen 300 mg/kg was intraperitoneally administered. After 24 hours, the blood was drawn from the abdominal aorta of each rat and the serum was separated and determined for s-GOT and GPT.

Results: The effect of seven glutathione derivatives on acetaminophen-induced liver damage was evaluated (Table 3). As a result, significant efficacy was found in compounds wherein $n=0$, $R_1=C_3H_7$ and $R_2=OH$, $OC_2H_5$, $OC_4H_9$ or $OC_3H_7$ and compounds wherein $R_1=H$ and $R_2=R_3=NH_2$ or $R_2R_3=NH$. Moreover, the compound in which $n=1$, $R_1=C_3H_7$ and $R_2=R_3=C_4H_9$ also showed a significant effect.

TABLE 3

Effect on Acetaminophen-induced liver damage

| Test substance (n = 0) | s-GOT | | s-GPT | |
|---|---|---|---|---|
| Physiological saline | 4375 ± 911 | | 1388 ± 316 | |
| $R_1 = C_3H_7$, $R_2 = R_3 = OH$ | 929 ± 500 *2 | (78.8) | 404 ± 278 *1 | (70.9) |
| $R_1 = C_3H_7$, $R_2 = R_3 = OC_2H_5$ | 394 ± 178 *2 | (91.0) | 111 ± 51 *2 | (92.0) |
| $R_1 = C_3H_7$, $R_2 = R_3 = OC_4H_9$ | 178 ± 64 *2 | (95.9) | 45 ± 11 *2 | (96.8) |
| $R_1 = C_3H_7$, $R_2 = R_3 = NH_2$ | 1760 ± 911 | (59.8) | 740 ± 394 | (46.7) |
| Physiological saline | 2802 ± 552 | | 704 ± 142 | |
| $R_1 = H$, $R_2 = R_3 = NH_2$ | 591 ± 155 *2 | (78.9) | 147 ± 48 *1 | (79.1) |
| $R_1 = H$, $R_2R_3 = NH$ | 1288 ± 316 *1 | (54.0) | 351 ± 82 *1 | (50.1) |

Each value is mean ± S.E. The number of cases is 7 to 10.
The figure in parentheses denotes the percent inhibition
Significant difference from saline control: *1: $p < 0.05$, *2: $p < 0.01$

| Test substance (n = 0) | s-GOT | | s-GPT | |
|---|---|---|---|---|
| Physiological saline | 2662 ± 559 | | 756 ± 175 | |
| $R_1 = C_3H_7$, $R_2 = R_3 = C_4H_9$ | 309 ± 105 *1 | (88.4) | 86 ± 31 | (70.9) |

Each value is mean ± S.E. The number of cases is 6.
The figure in parentheses denotes the percent inhibition.
Significant difference from saline control: *1: $p < 0.01$

FORMULATION EXAMPLE 1 Oral Tablet

| | |
|---|---|
| S-(1,2-Dicarbobutoxyethyl)GS isopropyl ester | 100 mg |
| Lactose | 80 mg |
| Starch | 17 mg |
| Magnesium stearate | 3 mg |

According to the above formula per tablet, tablets are manufactured by the established pharmaceutical procedure. If necessary, the tablets may be sugar-coated.

FORMULATION 2 Injection

| | |
|---|---|
| S-(1,2-Dicarbethoxyethyl)GS isopropyl ester | 1.5 g |
| Sodium chloride | 0.6 g |
| Distilled water for injection | 100 ml |

The above ingredient are admixed and aseptically filtered. The filtrate is aseptically filled in 2 ml portions in glass ampules, which are then sealed by fusion to provide an injectable solution.

FORMULATION EXAMPLE 3 Ophthalmic Solution

| | |
|---|---|
| S-(1,2-Dicarboxyethyl)GS isopropyl ester | 1.0 (W/V) % |
| Boric acid | 0.7 |
| Sodium acetate | 0.2 |
| Sodium chloride | 0.5 |

-continued

| | |
|---|---|
| Methyl p-hydroxybenzoate | 0.02 |
| Chlorobutanol | 0.3 |
| 10 (W/V) % sodium hydroxide | q.s. |
| Sterilized pure water | To make 100 ml |
| | pH 6.5 |

[Formulation Example 4] Ointment

| | |
|---|---|
| S-(1,2-Dicarbethoxyethyl)GS ethyl ester | 20 g |
| White petrolatum | 250 g |
| Stearyl alcohol | 200 g |
| Propylene glycol | 120 g |
| Polyoxyethylene-hydrogenated castor oil 60 | 40 g |
| Glycerol monostearate | 10 g |
| Methyl p-hydroxybenzoate | 1 g |
| Propyl p-hydroxybenzoate | 1 g |
| Purified water | To make 1000 g |

INDUSTRIAL UTILIZATION

The novel glutathione derivatives of the invention are excellent in tissue transfer kinetics and have antiinflammatory, antiallergic or hepatic disorders inhibitory activity. Therefore, they can be used advantageously as therapeutic agents for various diseases.

We claim:

1. A method for the treatment of an inflammatory, allergic or hepatic disorder which comprises administering to a patient in need of such treatment an effective amount of a compound of the formula

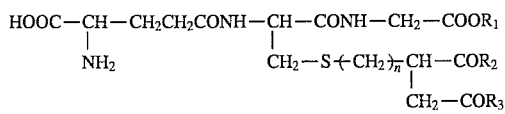

wherein
   n represents 0 or 1;
   $R_1$ is hydrogen or an alkyl group;
   $R_2$ and $R_3$ are the same or different and independently represent a hydroxyl group, a lower alkoxy group or an amino group, or $R_2$ and $R_3$ together form an imino group;
   provided that $R_1$ is an alkyl group when n is 0 and $R_2$ and $R_3$ are the same or different and independently are a hydroxyl group or a lower alkoxy group;
or a pharmaceutically acceptable salt thereof.

2. A compound of the formula

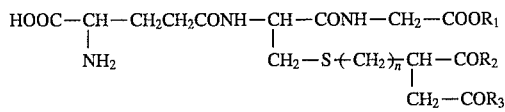

wherein
   n is 1;
   $R_1$ is hydrogen or an alkyl group; and
   $R_2$ and $R_3$ are amino;
or a pharmaceutically acceptable salt thereof.

3. A compound of the formula

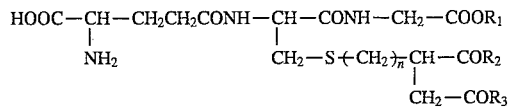

wherein
   n is 1;
   $R_1$ is hydrogen or an alkyl group; and
   $R_2$ and $R_3$ together are imino;
or a pharmaceutically acceptable salt thereof.

* * * * *